US011467393B2

(12) United States Patent
Jones et al.

(10) Patent No.: US 11,467,393 B2
(45) Date of Patent: Oct. 11, 2022

(54) ELLIPTICAL OPTICAL LENS FOR HIGH OUTPUT LED

(71) Applicant: Acera LLC, Beverly, MA (US)

(72) Inventors: Carlton Jones, Boxford, MA (US); Rachel Taranta, Somerville, MA (US); Thomas V. Root, Beverly, MA (US)

(73) Assignee: Acera, LLC, Beverly, MA (US)

( * ) Notice: Subject to any disclaimer, the term of this patent is extended or adjusted under 35 U.S.C. 154(b) by 228 days.

(21) Appl. No.: 15/337,922

(22) Filed: Oct. 28, 2016

(65) Prior Publication Data

US 2017/0123199 A1    May 4, 2017

Related U.S. Application Data

(60) Provisional application No. 62/247,456, filed on Oct. 28, 2015, provisional application No. 62/247,454, (Continued)

(51) Int. Cl.
*G02B 23/24* (2006.01)
*G02B 19/00* (2006.01)
(Continued)

(52) U.S. Cl.
CPC ........ *G02B 23/2453* (2013.01); *A61B 1/0011* (2013.01); *A61B 1/00126* (2013.01); (Continued)

(58) Field of Classification Search
CPC ... G02B 23/2453; F21V 29/773; F21V 29/89; F21V 23/0414; F21V 17/12; F21V 15/01; (Continued)

(56) References Cited

U.S. PATENT DOCUMENTS 2,908,197 A    10/1959  Wells
3,285,242 A    11/1966  Wallace
(Continued)

FOREIGN PATENT DOCUMENTS

CN    201680208 U    12/2010
CN    205079073 U    3/2016
(Continued)

OTHER PUBLICATIONS

Invitation To Pay Additional Fees for corresponding PCT Application No. PCT/US2016/059361, dated Feb. 3, 2017, 6 pages.
(Continued)

*Primary Examiner* — Rajarshi Chakraborty
*Assistant Examiner* — Nathaniel J Lee
(74) *Attorney, Agent, or Firm* — Potomac Law Group, PLLC (57) ABSTRACT

An elliptical lens comprises a lens body having a proximal section and a distal section. The proximal section has at least one input surface for receiving light from a light source and the distal section has at least one output surface through which light exits the lens body. The proximal section further comprises a substantially elliptical peripheral surface receiving at least a portion of the light entering the lens body via the at least one input surface and directing at least some of the received light via total internal reflection to the distal section such that at least a portion of the light directed to the distal section exits the lens body through said at least one output surface. Optical assemblies having said elliptical lens may be embedded in medical devices such as endoscopes to provide efficient illumination.

24 Claims, 6 Drawing Sheets

Related U.S. Application Data filed on Oct. 28, 2015, provisional application No. 62/247,451, filed on Oct. 28, 2015.

(51) Int. Cl.

| | | |
|---|---|---|
| G02B 6/42 | (2006.01) | |
| A61B 1/00 | (2006.01) | |
| A61B 1/06 | (2006.01) | |
| H05B 45/10 | (2020.01) | |
| G02B 1/04 | (2006.01) | |
| F21V 8/00 | (2006.01) | |
| F21V 29/77 | (2015.01) | |
| F21V 29/89 | (2015.01) | |
| F21L 4/00 | (2006.01) | |
| F21V 5/04 | (2006.01) | |
| F21V 15/01 | (2006.01) | |
| F21V 23/04 | (2006.01) | |
| F21V 23/06 | (2006.01) | |
| F21V 3/00 | (2015.01) | |
| F21V 17/12 | (2006.01) | |
| A61B 1/07 | (2006.01) | |
| G02B 6/38 | (2006.01) | |
| F21Y 115/10 | (2016.01) | |
| F21L 14/02 | (2006.01) | |
| F21W 131/20 | (2006.01) | |
| F21W 131/40 | (2006.01) | |

(52) U.S. Cl.
CPC ............ *A61B 1/0669* (2013.01); *F21L 4/005* (2013.01); *F21V 3/00* (2013.01); *F21V 5/04* (2013.01); *F21V 5/048* (2013.01); *F21V 15/01* (2013.01); *F21V 17/12* (2013.01); *F21V 23/0414* (2013.01); *F21V 23/06* (2013.01); *F21V 29/773* (2015.01); *F21V 29/89* (2015.01); *G02B 1/041* (2013.01); *G02B 6/0006* (2013.01); *G02B 6/0008* (2013.01); *G02B 6/4206* (2013.01); *G02B 6/428* (2013.01); *G02B 6/4231* (2013.01); *G02B 6/4269* (2013.01); *G02B 19/0066* (2013.01); *G02B 23/2469* (2013.01); *H05B 45/10* (2020.01); *A61B 1/00105* (2013.01); *A61B 1/07* (2013.01); *F21L 4/00* (2013.01); *F21L 14/02* (2013.01); *F21W 2131/20* (2013.01); *F21W 2131/40* (2013.01); *F21Y 2115/10* (2016.08); *G02B 6/3807* (2013.01)

(58) Field of Classification Search
CPC ... F21V 5/048; F21V 5/04; F21V 3/00; A61B 1/0011; A61B 1/00126; A61B 1/0669; F21L 4/005
See application file for complete search history.

(56) References Cited

U.S. PATENT DOCUMENTS

| | | | |
|---|---|---|---|
| 3,592,199 | A | 7/1971 | Ostensen |
| 4,414,608 | A | 11/1983 | Furihata |
| 4,726,074 | A | 2/1988 | Baclit et al. |
| D331,634 | S | 12/1992 | Browne |
| 5,353,208 | A | 10/1994 | Moore |
| 5,609,561 | A | 3/1997 | Uehara et al. |
| 5,682,199 | A | 10/1997 | Lankford |
| 5,702,349 | A | 12/1997 | Morizumi |
| 5,743,848 | A | 4/1998 | Koeda |
| 5,765,223 | A | 6/1998 | McCausland |
| 6,007,485 | A | 12/1999 | Koeda et al. |
| 6,099,147 | A | 8/2000 | Ziegenfuss |
| 6,135,947 | A | 10/2000 | Watanabe et al. |
| 6,257,741 | B1 | 7/2001 | Williams et al. |
| 6,540,389 | B1 | 4/2003 | Novak et al. |
| 6,819,505 | B1 | 11/2004 | Cassarly et al. |
| 6,937,791 | B2 | 8/2005 | Guy |
| 6,991,603 | B2 | 1/2006 | Krupa et al. |
| 7,115,091 | B2 | 10/2006 | Root et al. |
| D533,939 | S | 12/2006 | Root et al. |
| 7,193,519 | B2 | 3/2007 | Root et al. |
| 7,198,397 | B2 | 4/2007 | Bennett et al. |
| 7,229,201 | B2 | 6/2007 | Krupa et al. |
| D551,762 | S | 9/2007 | Root et al. |
| D561,336 | S | 2/2008 | Laflash et al. |
| D581,052 | S | 11/2008 | Root et al. |
| D623,786 | S | 9/2010 | Wessel |
| 7,798,692 | B2 | 9/2010 | Krupa et al. |
| D629,537 | S | 12/2010 | Hsu et al. |
| D631,567 | S | 1/2011 | Lodhie |
| 8,033,704 | B2 | 10/2011 | Krupa et al. |
| 8,152,715 | B2 | 4/2012 | Root et al. |
| D662,231 | S | 6/2012 | Sakamoto et al. |
| D663,445 | S | 7/2012 | Sakamoto et al. |
| D663,464 | S | 7/2012 | Lee |
| D666,340 | S | 8/2012 | Sakamoto et al. |
| D669,200 | S | 10/2012 | Chen et al. |
| D671,241 | S | 11/2012 | Sakamoto et al. |
| D671,242 | S | 11/2012 | Sakamoto et al. |
| D671,243 | S | 11/2012 | Sakamoto et al. |
| D675,349 | S | 1/2013 | Parker et al. |
| D685,506 | S | 7/2013 | Pickard et al. |
| D690,383 | S | 9/2013 | Sheikh et al. |
| 8,534,890 | B2 * | 9/2013 | Goto ............... G02B 19/0061 362/581 |
| 8,801,253 | B2 | 8/2014 | Krupa et al. |
| D715,463 | S | 10/2014 | Jun |
| 9,022,628 | B2 | 5/2015 | Krupa et al. |
| 9,055,863 | B2 | 6/2015 | Krupa et al. |
| D739,586 | S | 9/2015 | Hong |
| D744,674 | S | 12/2015 | Wu et al. |
| D753,322 | S | 4/2016 | Taylor |
| D760,928 | S | 7/2016 | Bao |
| D768,321 | S | 10/2016 | Inskeep |
| D775,752 | S | 1/2017 | Nook et al. |
| D778,473 | S | 2/2017 | Cooper |
| D793,595 | S | 8/2017 | Lesperance et al. |
| D804,064 | S | 11/2017 | Taylor et al. |
| D810,325 | S | 2/2018 | Guo |
| D813,424 | S | 3/2018 | Shum et al. |
| D836,227 | S | 12/2018 | Root |
| 10,281,709 | B2 | 5/2019 | Root et al. |
| 10,768,407 | B2 | 9/2020 | Root et al. |
| 10,782,518 | B2 | 9/2020 | Root et al. |
| 11,016,282 | B2 | 5/2021 | Root et al. |
| 2003/0009084 | A1 | 1/2003 | May et al. |
| 2003/0074708 | A1 | 4/2003 | Hogg |
| 2003/0091820 | A1 | 5/2003 | Robbins |
| 2003/0158503 | A1 | 8/2003 | Matsumoto |
| 2004/0213001 | A1 * | 10/2004 | Sayers ............... F21V 5/045 362/555 |
| 2004/0218858 | A1 * | 11/2004 | Guy ............... G02B 6/4206 385/33 |
| 2004/0246744 | A1 | 12/2004 | Krupa et al. |
| 2005/0162848 | A1 | 7/2005 | Dalton et al. |
| 2005/0201100 | A1 * | 9/2005 | Cassarly ............... F21V 29/713 362/317 |
| 2006/0183977 | A1 | 8/2006 | Ishigami et al. |
| 2007/0104664 | A1 | 5/2007 | Maltezos et al. |
| 2007/0173695 | A1 | 7/2007 | Hirata |
| 2007/0253188 | A1 | 11/2007 | Klipstein |
| 2008/0027408 | A1 | 1/2008 | Wilson et al. |
| 2008/0039715 | A1 | 2/2008 | Wilson et al. |
| 2008/0091064 | A1 | 4/2008 | Laser |
| 2008/0174996 | A1 | 7/2008 | Lu et al. |
| 2008/0194973 | A1 | 8/2008 | Imam |
| 2009/0040783 | A1 * | 2/2009 | Krupa ............... G02B 6/0006 362/555 |
| 2009/0185392 | A1 | 7/2009 | Krupa et al. |
| 2010/0226127 | A1 * | 9/2010 | Bigliatti ............... F21V 7/0091 362/327 |
| 2010/0277894 | A1 | 11/2010 | Kim |
| 2011/0194295 | A1 | 8/2011 | Householder |

(56) References Cited

U.S. PATENT DOCUMENTS

| | | |
|---|---|---|
| 2013/0046172 A1 | 2/2013 | Waitzman et al. |
| 2014/0148653 A1 | 5/2014 | McMahon et al. |
| 2015/0219313 A1 | 8/2015 | Marcaly |
| 2016/0050990 A1 | 2/2016 | Hayes |
| 2017/0122525 A1 | 5/2017 | Root et al. |
| 2017/0123131 A1 | 5/2017 | Root et al. |
| 2017/0123199 A1 | 5/2017 | Jones et al. |
| 2017/0197002 A1 | 7/2017 | Dobrinsky et al. |
| 2019/0361217 A1 | 11/2019 | Root et al. |
| 2020/0081241 A1 | 3/2020 | Root et al. |
| 2020/0205640 A1 | 7/2020 | Miike et al. |
| 2021/0278657 A1 | 9/2021 | Root et al. |
| 2021/0299298 A1 | 9/2021 | Root et al. |
| 2021/0307421 A1 | 10/2021 | Root et al. |

FOREIGN PATENT DOCUMENTS

| | | |
|---|---|---|
| EP | 2846179 A2 | 3/2015 |
| JP | S56-59005 A | 5/1981 |
| JP | H4-288960 A | 10/1992 |
| JP | H8-10220 A | 1/1996 |
| JP | 2000171725 A | 6/2000 |
| JP | 3148028 B2 | 3/2001 |
| JP | 2002345748 A | 12/2002 |
| JP | 200791119 A | 4/2007 |
| JP | 2013123477 A | 6/2013 |
| JP | 2015077336 A | 4/2015 |
| KR | 20190067110 A | 6/2019 |
| WO | 2008016895 A2 | 2/2008 |
| WO | 2008017718 A1 | 2/2008 |
| WO | 2010091097 A1 | 8/2010 |
| WO | 2015038971 A1 | 3/2015 |

OTHER PUBLICATIONS

International Search Report/Written Opinion for corresponding PCT Application No. PCT/US2016/059361, dated Apr. 4, 2017, 16 pages.
International Preliminary Report on Patentability for corresponding PCT Application No. PCT/US2016/059361, dated May 11, 2018, 10 pages.
International Search Report/Written Opinion for corresponding PCT Application No. PCT/US2016/059406, dated Apr. 7, 2017, 11 pages.
Invitation To Pay Additional Fees and, Where Applicable, Protest Fee, for PCT/US2016/059451, dated Mar. 16, 2017; 6 pages.
International Search Report/Written Opinion for corresponding PCT/US2016/059451, dated Jun. 19, 2017; 15 pages.
European Search Report, 16794163.2, dated Jan. 7, 2020, 7 pages.
Japanese Office Action, JP2018-542988, dated Sep. 1, 2021, 4 pages.
European Examination Report, 16794169.9, dated Nov. 17, 2021, 10 pages.
International Invitation to Pay Additional fees and Partial Search Report, PCT/US2021/022948, dated Jun. 29, 2021, 13 pages.
International Search Report and Written Opinion, PCT/US2021/022948, dated Aug. 19, 2021, 21 pages.
U.S. Appl. No. 17/328,827, filed May 24, 2021, Root, et al.
U.S. Appl. No. 17/205,529, filed Mar. 18, 2021, Root, et al.
U.S. Appl. No. 17/220,266, filed Apr. 1, 2021, Root, et al.
International Search Report and Written Opinion, PCT/US2019/069111, dated Mar. 25, 2020, 24 pages.
International Search Report and Written Opinion, PCT/US2021/025050, dated Jul. 6, 2021, 13 pages.
Japanese Office Action, JP2018-542993, dated May 12, 2021, 15 pages.
European Examination Report, 16798028.3, dated Jul. 1, 2021, 4 pages.
International Preliminary Report on Patentability for corresponding PCT Application No. PCT/US2019/069111, dated Jun. 16, 2021, 6 pages.
Japanese Office Action, JP2018-542988, dated Oct. 21, 2020, 10 pages.
Japanese Office Action, JP2018-542993, dated Oct. 14, 2020, 14 pages.
European Extended Search Report, 21164168.3, dated Apr. 23, 2021, 7 pages.
U.S. Appl. No. 16/731,852, filed Dec. 31, 2019, Shinya Miike.
Japanese Office Action, JP2018-542988, dated Mar. 30, 2022, 9 pages.

\* cited by examiner

ELLIPTICAL OPTICAL LENS FOR HIGH OUTPUT LED

RELATED APPLICATIONS

The present application claims priority to a provisional application entitled "Elliptical optical lens for high output LED" having an application No. 62/247,451 filed on Oct. 28, 2015, which is herein incorporated by reference in its entirety. The present application also claims priority to a provisional application entitled "Embeddable module for high output LED" having an application No. 62/247,454 filed on Oct. 28, 2015, and a provisional patent application entitled "Handheld mobile light source" having an application No. 62/247,456 filed on Oct. 28, 2015, both of which are herein incorporated by reference in their entirety.

The present application is also related to utility applications entitled "Embeddable module for high output LED" and "Handheld mobile light source," which are being filed concurrently herewith and which are herein incorporated by reference in their entirety.

TECHNICAL FIELD

The present disclosure relates generally to optical lenses and more specifically to elliptical optical lenses that capture and transmit light with high efficiency.

BACKGROUND

Many devices that operate in small, closed areas, require a light source to operate. For example, laparoscopic and endoscopic procedures are conducted through small incisions in the skin or natural body orifices. In order to operate or view an internal area, medical professionals use endoscopes that have small, elongated distal portions that fit within these small openings but are long enough to reach the internal areas within the body. These instruments need to provide precise and accurate movement in order to reach areas within the body that are difficult to access. The distal working ends of the endoscopes usually contain a small camera that allows a medical professional to view the internal area within the body during the procedure. This camera and the working end of the endoscope must have adequate remotely controlled illumination to permit the medical professional to view the internal area. In some endoscopes, a camera positioned outside the patient's body can receive, via a light guide, radiation reflected from an illuminated internal area and form an image of that area for viewing by a medical professional.

Conventional light sources for devices such as endoscopes are burdensome, very inefficient in converting electrical power to light, produce large amounts of heat that must be dissipated, and require that the devices be connected to external light sources, limiting the range of motion. For example, incandescent lamps produce light by passing current through a highly flexible, elongated, tungsten filament, causing the entire filament to radiate light in proportion to its temperature. Arc lamps produce light by creating plasma between two electrodes within a sealed bulb. Both types of lamps produce too much heat and must be connected to large external light sources.

Light sources that produce much less heat, such as light emitting diodes (LEDs), usually do not produce enough illumination to effectively assist a device such as an endoscope. One approach to increase this low level of light is by coupling multiple light emitting diodes (LEDs) to long, flexible fiber optic light guides. Many LEDs must be used due to low light output emitted by LEDs into the optical fiber. Another approach for bolstering the low light output between LEDs and optical fibers is to utilize various combinations of lenses, mirrors, or prisms in order to collect and focus LED-generated light into the optical fiber. A further approach for bolstering the low light output is to couple multiple optical fibers to separate LEDs, so as to produce a greater cumulative light output.

However, each of these conventional approaches can result in ineffective illumination for most lighting applications. For example, light loss due to inefficient coupling between the LED and the optical fiber can limit the amount of light transmitted between them. In addition, non-rigid, non-mechanical attempts to increase the efficiency between LEDs and optical fibers can prevent interchangeability of an illumination device and necessitate a complex alignment procedure between the LED and the optical fiber.

Accordingly, there is a need for optical lenses that efficiently capture and focus light for transmission to a light guide.

SUMMARY

According to one aspect, a lens is disclosed, which comprises a lens body comprising a proximal section having at least one input surface for receiving light from a light source and a distal section having at least one output surface through which light exits the lens body. The proximal section further comprises a substantially elliptical peripheral surface receiving at least a portion of the light entering the lens body via said at least one input surface and directing at least some of said received light via total internal reflection to said distal section such that at least a portion of the light directed to the distal section exits the lens body through said at least one output surface.

In some embodiments, the peripheral elliptical surface may be characterized by a proximal focal point and a distal focal point and may be shaped such that said distal focal point is positioned outside of said distal section of the lens body.

In some embodiments, said distal focal point may be positioned at a distance in a range of about 4 mm to about 6 mm relative to the output surface. In some embodiments, the distal focal point may be positioned inside said lens body. In some embodiments, the distal focal point may be positioned at a distance in a range of about 4 mm to about 6 mm below said output surface. In some embodiments, the proximal focal point of the elliptical surface may be positioned at or in proximity of the light source such that the elliptical surface transfers at least a portion of the light emitted by the light source from the proximal focal point to the distal focal point.

In some embodiments, the input surface of the lens can comprise a central convex portion and a peripheral portion surrounding said central convex portion.

In some embodiments, the input surface of the lens can form a surface of a cavity configured to receive at least partially the light source. In some embodiments, the proximal focal point of the elliptical surface may be disposed within said cavity.

In some embodiments, the peripheral portion of the input surface may be shaped such that at least a portion of the light entering the lens body via said peripheral portion propagates to the peripheral elliptical surface to be reflected thereby. In some embodiments, the peripheral portion of the input surface may be shaped such that at least about 80% of the light entering the lens body via the peripheral portion propagates to the peripheral surface of the lens body.

In some embodiments, the convex portion of the input surface can be characterized by a positive optical power in a range of about 50 D to about 300 D. In some embodiments, at least a portion of the light entering the lens body via the convex portion propagates to the output surface. In some embodiments, the convex portion may be configured such that the light entering the lens body via the convex portion propagates to the output surface without striking the elliptical peripheral surface. In some embodiments, the peripheral portion of the input surface may comprise a proximal concave segment and distal convex segment.

In some embodiments, the input surface may be configured to capture at least about 70%, or at least about 80%, or at least about 90%, or at least about 95% (and preferably 100%) of the light emitted by the light source. In some embodiments, the input surface may be configured to capture at least about 90% of the light emitted by said light source.

In some embodiments, the proximal section and said distal section may be disposed about an optical axis of the lens body. In some embodiments, the output surface may be substantially flat. In some embodiments, the output surface may be substantially orthogonal to said optical axis.

In some embodiments, the lens may further comprise a collar at least partially surrounding the lens body. In some embodiments, the collar may be disposed at a boundary between said proximal section and said distal section. In some embodiments, the proximal and distal sections may form a unitary structure. In some embodiments, the proximal and distal sections and the collar may form a unitary structure.

In some embodiments, the lens body and collar may be formed of a polymeric material. In some embodiments, said polymeric material may be any of polycarbonate, polymethylmethacrylate (PMMA), and high density polyethylene. In some embodiments, any of said lens body and said collar may be formed of any of glass and silicone.

According to another aspect, there is disclosed an optical assembly comprising a lens having a lens body comprising a proximal section having at least one input surface for receiving light from a light source, and a distal section having at least one output surface through which light exits the lens body. The optical assembly further comprises a light guide optically coupled to said output surface of the lens body for receiving at least a portion of the light exiting the lens. The proximal section further comprises a substantially elliptical peripheral surface receiving at least a portion of the light entering the lens body via said at least one input surface and directing at least some of the received light via total internal reflection to said distal section such that at least a portion of the light directed to the distal section exits the lens body through said at least one output surface. In some embodiments, the light guide may be attached to the output surface of the lens. In some embodiments, the peripheral elliptical surface may be characterized by a proximal focal point and a distal focal point and may be shaped such that the distal focal point is positioned outside of said distal section of the lens body.

In some embodiments, said distal focal point may be positioned at a distance in a range of about 4 mm to about 6 mm relative to said output surface. In some embodiments, the proximal focal point of said elliptical surface may be positioned substantially at or in proximity of the light source such that the elliptical surface transfers at least a portion of light emitted by the light source from the proximal focal point to the distal focal point. In some embodiments, the input surface may comprise a central convex portion and a peripheral portion surrounding said central convex portion. In some embodiments, the peripheral portion of the input surface may be shaped such that at least a portion of the light entering the lens body via said peripheral portion propagates to the peripheral elliptical surface to be reflected thereby. In some embodiments, the convex portion may be characterized by a positive optical power in a range of about 50 D to about 300 D. In some embodiments, the peripheral portion of the input surface may comprise a proximal concave segment and distal convex segment.

In some embodiments of the above optical assembly, the input surface may be configured to capture at least about 70%, or at least about 80%, or at least about 90% (and preferably 100%) of the light emitted by said light source. In some embodiments, said lens may further comprise a collar encircling at least partially the lens body. In some embodiments, the lens body and said collar may be formed as a unitary structure.

According to another aspect, there is disclosed a lens comprising a lens body, which includes an input surface for receiving light from a light source, an output surface through which light exits the lens body, and an elliptical peripheral surface for receiving at least a portion for the light entering the lens body via said input surface and directing said received light via total internal reflection to said output surface. In some embodiments, the lens may further comprise a collar at least partially encircling the lens body.

In some embodiments, the elliptical surface may be characterized by an input focus and output focus. In some embodiments, the input focus may be positioned at or in proximity of the light source. In some embodiments, the output focus may be positioned outside of the lens body. In some embodiments, the output focus may be positioned within the lens body. In some embodiments, the input surface may comprise a convex central portion and a peripheral portion surrounding said central portion.

According to another aspect, there is disclosed an optical assembly, comprising a lens having a lens body comprising an input surface for receiving light from a light source, an output surface through which the light exits the lens body, and an elliptical peripheral surface for receiving at least a portion for the light entering the lens body via said input surface and directing said received light via total internal reflection to said output surface. The optical assembly further comprises a light guide optically coupled to the output surface of the lens body for receiving at least a portion of the light exiting the lens. In some embodiments, said lens further comprises a collar at least partially encircling said lens body.

The present disclosure is not limited to the particular embodiments described in this application, which are intended as illustrations of various aspects. Many modifications and variations can be made without departing from its spirit and scope, as will be apparent to those skilled in the art.

Further understanding of various aspects of the disclosure can be obtained by reference to the following detailed description in conjunction with the associated drawings, which are described briefly below.

DETAILED DESCRIPTION

It is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The term "optical power" is used herein consistent with its common meaning in the art to refer to the degree to which an optical component or surface converges or diverges incident light and is equal to the reciprocal of the focal length of the component of the surface.

The term "numerical aperture" is used herein consistent with its common meaning in the art to refer to a dimensionless number that characterizes the range of angles over which an optical component or system can emit or accept light.

The term "elliptical surface" or similar terms as used herein refer to a surface that is shaped as a section of an ellipse. In other words, an elliptical surface is in the form of a truncated ellipse.

The term "about" as used herein is intended to indicate a variation of at most 10% around a numerical value.

The term "substantially" is defined herein as at least close to (and may include) a given value or state, as understood by a person of ordinary skill in the art. In one embodiment, the term "substantially" refers to ranges within 10%, preferably within 5%, more preferably within 1%, and most preferably within 0.1% of the given value or state being specified.

According to aspects of the present disclosure, there is disclosed embodiments of an elliptical lens configured to capture most of the light emitted by a light source such as an LED light source, and to converge the light onto an output surface for efficient transmission to a light guide.

Embodiments of the lens disclosed herein may be easily adapted for use with different types of illumination devices, such as different endoscopes. In many embodiments, optical assemblies including an LED light source and an elliptical lens as disclosed herein, can provide higher illumination near the distal working end of an illumination device, with less power and less heat produced. Small batteries may be used to power the LED light source, permitting the illumination device to be compact and to operate without connection to an external light source.

Figure 1:
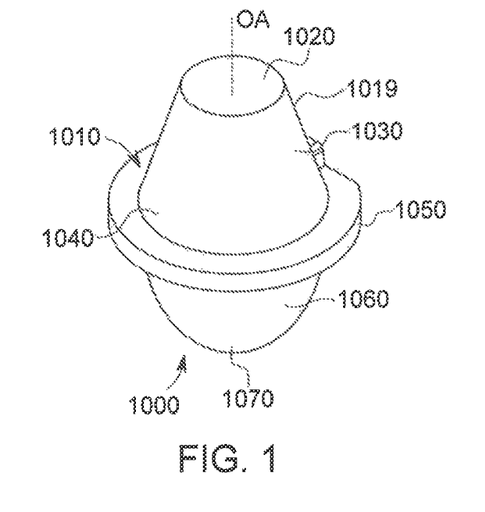
FIG. 1 is a top perspective view of one embodiment of an elliptical optic LED lens according to aspects of the present disclosure.
Figure 2:
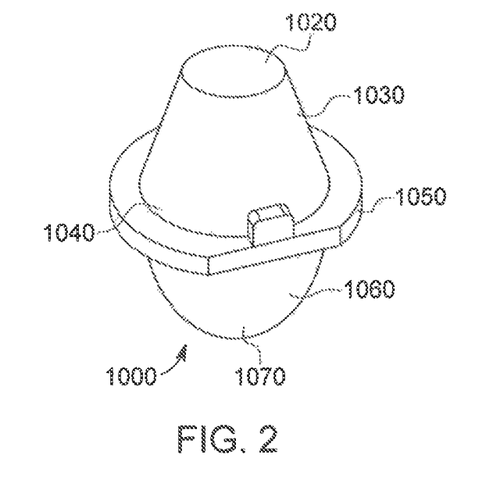
FIG. 2 is another top perspective view of the elliptical lens of FIG. 1 according to aspects of the present disclosure.
Figure 3:
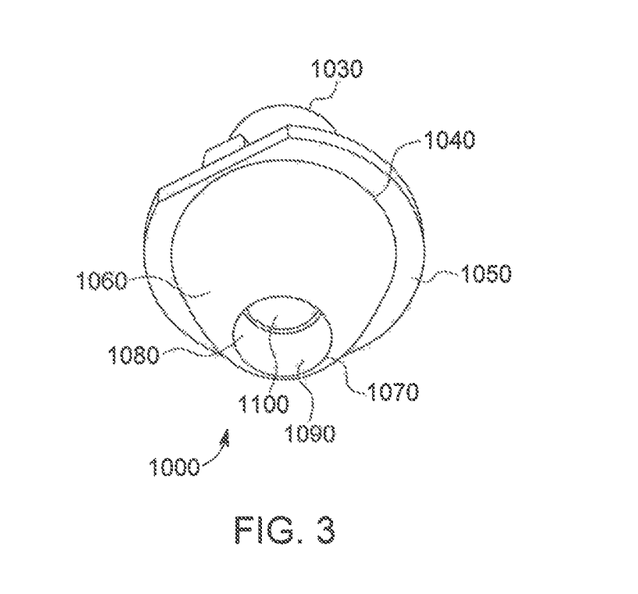
FIG. 3 is a bottom perspective view of the elliptical lens of FIG. 1 according to aspects of the present disclosure.

FIGS. 1, 2 and 3 show perspective views of one embodiment of a lens 1000 (herein also referred to as an elliptical lens) according to aspects of the present disclosure. The lens 1000 comprises a lens body 1010 disposed about an optical axis OA and having a distal section 1030 and a proximal section 1060. The proximal section 1060 includes an input surface 1070 for receiving light from a light source. In some embodiments, the proximal section 1060 may include a plurality of input surfaces. The distal section 1030 includes an output surface 1020, through which light exits the lens body 1010 and a peripheral portion 1019 that has a truncated conical shape in this embodiment, though other shapes can also be employed. In some embodiments, the distal section 1030 may include a plurality of output surfaces. The elliptical lens 1000 is configured to efficiently capture light emitted, for example, by an LED light source, and to transfer it onto a light guide coupled to the output surface 1020 (as shown and discussed with reference to FIG. 9).

The proximal section 1060 further comprises a substantially elliptical peripheral surface 1040, which is configured to receive at least a portion of the light entering the lens body 1010 via the input surface 1070. The elliptical surface 1040 is configured to direct at least a portion of the received light via total internal reflection to the distal section 1030, such that at least a portion of the light directed to the distal section exits the lens body 1010 through the output surface 1020. In some embodiments, the elliptical surface 1040 reflects at least about 80%, or at least about 90% (and preferably 100%) of the light incident thereon.

The lens 1000 can include a collar 1050 (herein also referred to as flange) coupled to the lens body 1010, as shown for example in FIG. 1. The flange may be positioned, for example, at a central section of the lens that has a wider diameter, and may be configured to facilitate holding the lens 1000 within an illumination device. In this embodiment, the flange 1050 is disposed at a boundary between the proximal section 1060 and the distal section 1030 of the lens.

In some embodiments, the proximal section 1060 and the distal section 1030 may form a unitary structure. In other embodiments, the proximal section 1060, the distal section 1030 and the flange 1050 may form a unitary structure.

The distal portion 1030 of the elliptical lens 1000 may be cone-shaped, tapering from a wider central diameter to a substantially planar output surface 1020 having a smaller diameter.

FIG. 3 is a bottom perspective view of the elliptical lens 1000, further illustrating the proximal section 1060. The proximal section 1060 includes the input surface 1070. In this embodiment, the input surface 1070 forms the surface of a cavity 1080 configured to receive at least partially a light source. The input surface 1070 comprises a central convex portion 1100 and a peripheral portion 1090.

In some embodiments the convex portion 1100 exhibits a positive optical power in a range of about 50 D to about 300 D.

Figure 4:
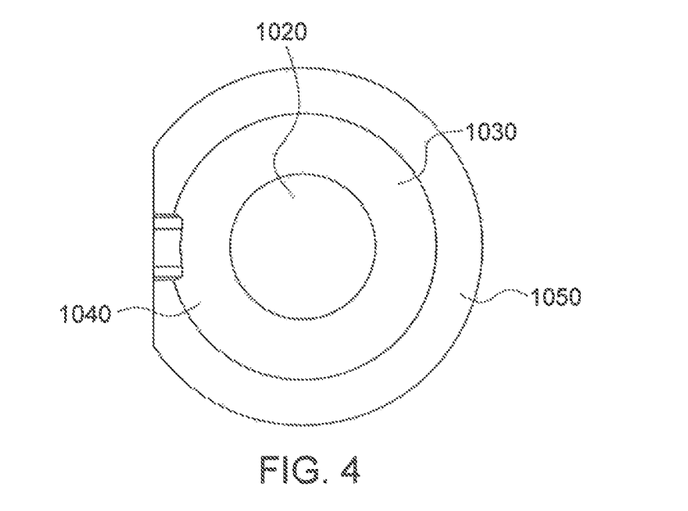
FIG. 4 is a top view of the elliptical lens of FIG. 1 according to aspects of the present disclosure.
Figure 5:
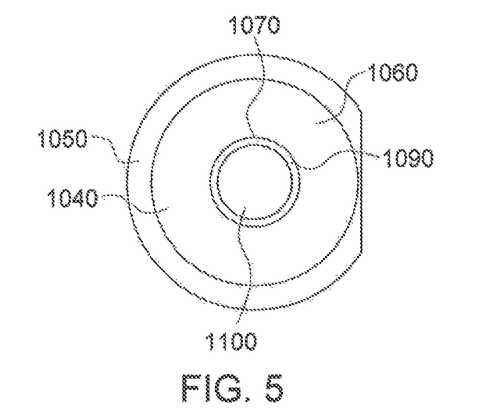
FIG. 5 is a bottom view of the elliptical lens of FIG. 1 according to aspects of the present disclosure.

FIG. 4 is a top view of the elliptical lens 1000, showing the distal section 1030 and the output surface 1020. FIG. 5 is a bottom view of the elliptical lens 1000, showing the proximal section 1060 having the input surface 1070, which is composed of the convex portion 1100 and the peripheral portion 1090.

Figure 6:
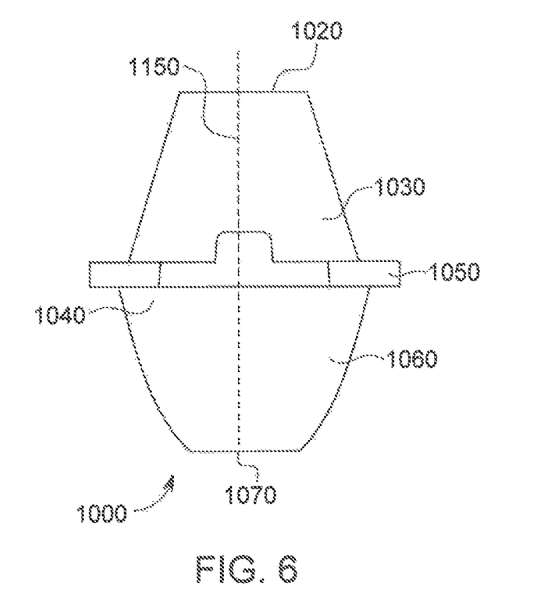
FIG. 6 is a side view of the elliptical lens of FIG. 1 according to aspects of the present disclosure.

FIG. 6 shows a side view of the lens 1000. The proximal section 1060 and the distal section 1030 may be disposed about an optical axis 1150 of the lens body 1010. In this embodiment, the output surface 1020 is substantially flat and is substantially orthogonal to the optical axis 1150.

Figure 7:
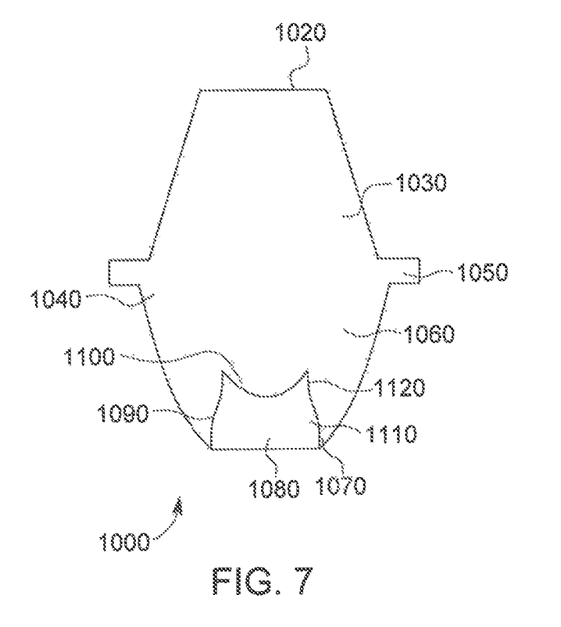
FIG. 7 is a side cross-sectional view of the elliptical lens of FIG. 1 according to aspects of the present disclosure.
Figure 8:
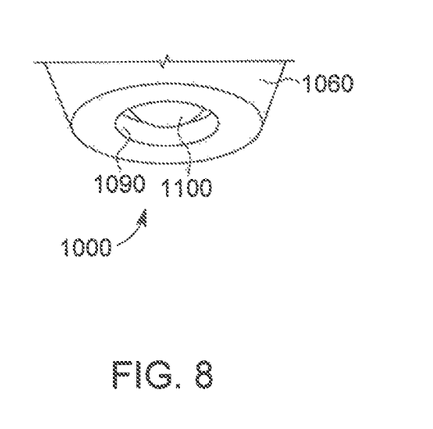
FIG. 8 is a bottom lateral cross-sectional view of the elliptical lens of FIG. 1 according to aspects of the present disclosure.

FIG. 7 shows a cross-sectional side view of the elliptical lens 1000 according to aspects of the present disclosure. In FIG. 7, the proximal section 1060 is shown to include the input surface 1070. The input surface 1070 defines a cavity 1080 configured to receive at least partially a light source, such as an LED (not shown). As noted above, the input surface 1070 comprises a central convex portion 1100 and a peripheral portion 1090. In this embodiment, the peripheral portion 1090 includes a proximal concave segment 1110 and a distal convex segment 1120. FIG. 8 is a bottom lateral view of the elliptical lens 1000, further showing the convex portion 1100 and the peripheral portion 1090 of the input surface 1070.

In some embodiments, the input surface 1070 can collect at least about 70%, or at least a about 80%, or at least about 90%, or at least about 95% (and preferably 100%) of the light emitted by a light source (such as an LED) that is optically coupled to the cavity formed by the input surface.

As noted above, in some embodiments, the convex portion 1100 may be characterized by a positive optical power, for example in a range of about 50 D to about 300 D. In various embodiments, the convex portion 1100 of the input surface converges the light entering the lens body via that portion such that at least a portion of the light (in many cases all the light) entering the lens body 1010 via the convex portion 1100 propagates to the output surface 1020 without striking the peripheral elliptical surface 1040.

The peripheral portion 1090 of the input surface 1070 is shaped such that at least a portion of the light entering the lens body 1010 via the peripheral portion propagates to the elliptical peripheral surface 1040 to be reflected thereby. For example, in one embodiment, the peripheral portion 1090 may be shaped such that at least about 80%, or at least 90%, or at least 95% (and preferably 100%), of the light entering the lens body 1010 via the peripheral portion propagates to the peripheral surface 1040.

In some embodiments, the reflection of the light rays incident on the elliptical peripheral surface 1040 can result in mixing of those light rays, thereby improving color-over-angle uniformity of the light exiting the lens relative to the respective color-over-angle uniformity of the light emitted by the light source. By way of example, in some embodiments, the lens 1000 can improve the color-over-angle uniformity of the light it receives from a light source by at least about 20%, or by at least about 30%, or by at least about 40%, or by at least about 50%, or by at least about 60%.

In various embodiments, the lens 1000 may be formed of a transparent material that allows light to pass through. For example, the lens 1000 may be composed of glass, plastic, or sapphire. In some embodiments, any one or more of the lens body and the flange may be formed of a polymeric material. In some embodiments, any one or more of the lens body and the flange may be formed of glass or silicone. Some suitable materials for forming the lens include, without limitation, polymethylmethacrylate (PMMA) and polycarbonate.

Figure 9:
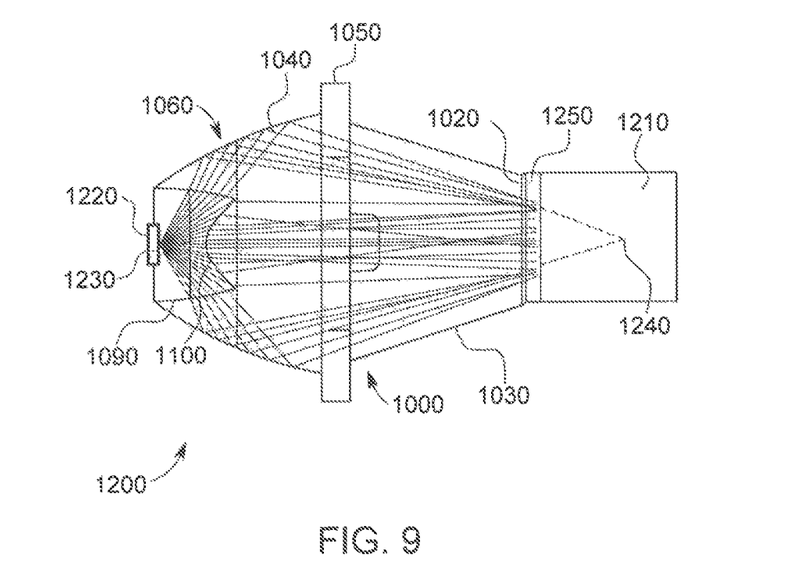
FIG. 9 shows propagation of light through an optical assembly including the elliptical lens of FIG. 1 according to aspects of the present disclosure.

The elliptical lens 1000 is configured to efficiently receive and transmit high output light to an illumination device. By way of example, FIG. 9 shows an optical assembly 1200 including the lens 1000. The optical assembly 1200 further comprises a light guide 1210 coupled to the output surface 1020 of the lens 1000 for receiving light existing the lens. For example, the light guide 1210 can be a single optical fiber, a bundle of optical fibers (e.g., a plurality of square or round-shaped optical fibers), a liquid light guide, a plurality of tapers made from glass or plastic to form a light guide, etc.

The optical assembly 1200 further includes a light source 1220, such as an LED, which is placed at least partially within the cavity 1080 defined by the input surface 1070. In one embodiment, the light source may be a high power LED (such as Luxeon III Model LXHL-LW3C) with a typical forward voltage of 3.7V and operating current at 700 mA. This device may be safely operated up to a current of 1 A with a corresponding typical forward voltage of 3.9V. The LED has a typical color temperature of 5500K.

This LED has an emitting surface of approximately 1 mm×1 mm, and is coated with a wavelength conversion phosphorus or fluorophore that emits a broadband continuum of visible white light between about 470-700 nm. This LED spreads the emitted light over a 160-degree angle (an angle at which 90% of the total illumination is captured). In various embodiments, any LED may be used with the lens 1000, including for example LEDs emitting radiation in the ultraviolet, visible (e.g., 530 nm), near infrared, and infrared regions of the electromagnetic spectrum. In some embodiments, the LED may have a power consumption of about 1 to 5 W. In some embodiments, the light source may include a plurality of LEDs providing light at the same or different wavelengths.

The elliptical lens 1000 is configured to collect the light emitted by the LED 1220 over a large angular spread and to converge that light so as it can be efficiently coupled to the light guide 1210 of an illumination device. For example, the elliptical lens 1000 can receive light emitted by the LED that is characterized by a maximum angular spread of about 160 degrees and reduce that maximum angular spread to about 66 degrees for coupling to the light guide 1210. In some such embodiments, the numerical aperture associated with the output surface of the lens 1000 can be in a range of about 0.5 to about 0.9, e.g., about 0.66 or about 0.88.

With continued reference to FIG. 9, the peripheral elliptical surface 1040 of the lens 1000 is characterized by a proximal focal point 1230 (herein also referred to as the input focus or input focal point) and a distal focal point 1240 (herein also referred to as the distal focus, distal focal point, or the output focus). In this embodiment, the proximal and distal focal points are positioned on the optical axis of the lens.

The peripheral elliptical surface transfers at least a portion of the light emitted by the light source 1220 from the proximal focal point to the distal focal point. In this embodiment, the proximal focal point is positioned within the input cavity and substantially at the light source 1220. Further, in this embodiment, the distal focal point 1240 is positioned external to the lens at a distance outside the output surface 1020 of the lens 1000. In some embodiments, the position of the distal focal point 1240 is selected such that the light rays diverging from the distal focal point exhibit an angular spread across the input face of a light guide coupled to the lens that maximizes the coupling of the light into the light guide. For example, the diverging beam can have an angular spread commensurate with an input numerical aperture of the light guide. For example, the distance between the distal focal point 1240 and the output surface of the lens may be in the range of about 4 mm to about 6 mm, though other values can also be used depending, for example, on the lens size and/or particular application in which the lens is employed. In this embodiment, the elliptical peripheral surface is shaped such that the distal focal point 1240 is positioned within the light guide proximate to its input surface so as to facilitate efficient coupling of the light exiting the lens into the light guide. In other embodiments, the distal focal point 1240 may be positioned inside the lens (e.g., below the output surface 1020) or may be positioned at the output surface 1020 of the lens.

In this embodiment, the light guide 1210 has a flat face, substantially filling the entire emitting area of the output surface 1020 of the elliptical lens 1000. The light guide 1210 may be placed in contact with, or substantially close to, the output surface 1020 of the elliptical optic lens 1000. In some embodiments, both the output surface 1020 and a surface of the light guide 1210 may be substantially flat, thereby allowing good contact therebetween. The flexibility of the light guide may also assist in achieving a higher degree of contact between the two surfaces. In this embodiment, the substantially planar output surface 1020 of the elliptical lens 1000 is index matched with the input face of the light 1210 by disposing a refractive index matching material 1250 therebetween. By way of example, the index matching material can be a liquid, a gel, an adhesive, or any other suitable material. The index matching material can minimize the reflection of the light at the interface between the output surface of the lens and the input face of the light guide, thereby enhancing the efficiency of the coupling of the light into the light guide.

With continued reference to FIG. 9, in some embodiments, the elliptical lens may capture light emitted from the LED without direct contact with the LED. By way of example, the LED may be disposed at a distance of less than about 3 mm or less than about 2 mm, e.g., at a distance of about 2.4 mm, from the convex portion of the lens' input surface.

In use, the input surface of the lens 1000 captures the light emitted by the LED 1220. A portion of that light enters the lens body via refraction at the peripheral portion 1090 of the input surface and another portion of that light enters the lens body via refraction at the central convex portion 1100 of the input surface. The light entering the lens body via the peripheral portion of the input surface propagates to the elliptical peripheral surface 1040 and is reflected thereby toward to the output focus 1240, which in this embodiment is located within a proximal portion of the light guide. As such, this reflected light exits the lens as a convergent bundle of rays to reach the output focus 1240 and then diverge beyond that point within the light guide. In some other embodiments, the output focus 1240 can be located internal to the lens such that the light rays reflected by the elliptical surface converge to arrive at the output focus 1240 and then diverge to reach the input face of the light guide. As noted above, in some such embodiments, the location of the output face 1240 can be selected such that the rays reaching the input face of the light guide have a maximum angular spread corresponding to that of a solid angle subtended by the input face of the light pipe for effective coupling of the light into the light pipe.

The portion of the light rays entering the lens body via refraction at the central convex portion 1100 of the input surface propagates through the lens body without striking the peripheral surface 1040 to reach the output surface 1020 through which it exits the lens. As noted above, in this embodiment the central convex portion of the input surface provides a positive optical power, which results in the convergence of the light rays entering the lens body through that surface to a focal point (herein also referred to as the convergence point) typically located within the lens body, e.g., a small distance below the lens' output surface. In some other embodiments, the convex portion is configured such that its focal point (i.e., the point at which the light rays refracted by that portion converge) is external to the lens. By way of example, the focal point of the convex portion may be within the proximal end of a light guide coupled to the lens, or external to both the lens and the light pipe such that the light rays diverging form the focal point to illuminate the input face of the light pipe would exhibit a maximum angular spread corresponding to that of a solid angle subtended by the input face of the light guide. By way of example, in some such embodiments, the focal point of the convex portion can be substantially coincident with the distal focal point of the elliptical peripheral surface.

The elliptical lens may be embedded and easily adapted for use with different types of illumination devices. In various embodiments, the elliptical optic lens may be embedded within medical or industrial endoscopes, video cameras, retractors, speculums, surgical headlights and other devices requiring high intensity, high quality light. In some embodiments, the elliptical lens may be removably and replaceably contained within an illumination device.

In various embodiments, the elliptical lens captures and transmits the LED light without relying on mirrors, other lenses, or multiple LEDs. The lack of such additional optical components (such as additional optics between the LED light source and the lens) simplifies the mechanical design and volume occupied by the lens for easier incorporation into a variety of illumination devices.

The LED light source is very efficient in converting electrical energy into light, allowing small batteries to be used to power the LED, thereby permitting the illumination device to operate without connection to an external light source. Accordingly, optical assemblies disclosed herein may operate for a considerable length of time without the need for battery replacement or recharging, and without making the illumination device cumbersome or unwieldy. As a result, illumination devices in accordance with the presence invention can be small and compact while providing the desired illumination strength.

Figure 10:
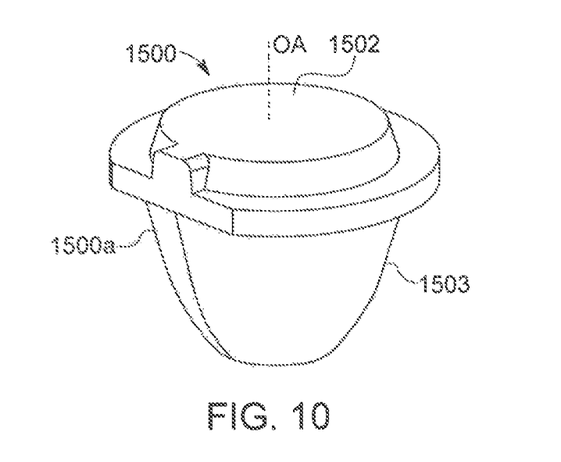
FIG. 10 is a schematic perspective view of a lens according to another embodiment of the present teachings.

FIG. 10 schematically depicts a lens 1500 according to another embodiment, which includes a lens body 1500*a* disposed about an optical axis (OA) and having an input surface 1501, an output surface 1502 and a peripheral surface 1503.

Figure 11:
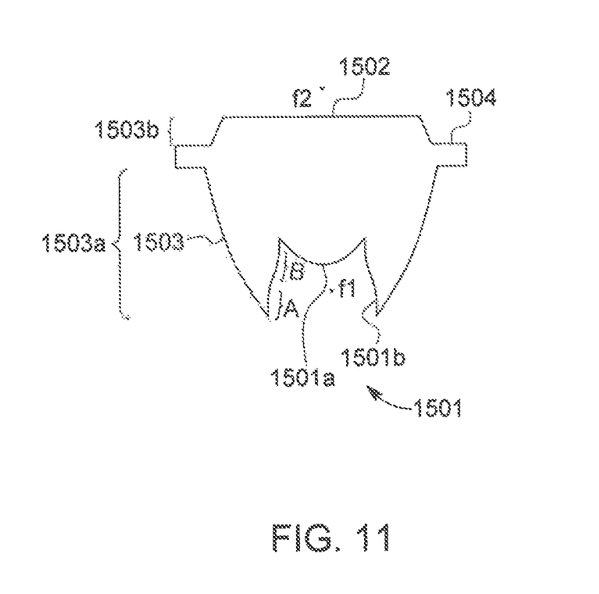
FIG. 11 is a schematic cross-sectional view of the lens depicted in FIG. 10.

Similar to the previous embodiment, the input surface 1501 is composed of a central convex portion 1501*a* and a peripheral portion 1501*b*, which collectively form a cavity for at least partially receiving a light source. In this embodiment, the peripheral portion 1501*b* includes a proximal concave segment (A) and a distal convex segment (B). A collar 1504 disposed in proximity of the output surface 1502 partially encircles the lens body. Similar to the previous embodiment, the collar 1504 facilitates positioning the lens within a light illumination device.

Further, similar to the previous embodiment, the peripheral surface 1503 of the lens is in the form of a truncated ellipse having an input focus f1 and an output focus f2. In this embodiment, the input focus f1 is positioned within the input cavity and the output focus f2 is positioned external to the lens body at a distance from the output surface, e.g., at a distance in a range of about 4 mm to about 6 mm from the output surface. In other embodiments, the output focus f2 can be positioned within the lens body, e.g., at a small distance below the output surface, or at the output surface.

In some embodiments, the elliptical peripheral surface 1503 can extend from the input surface of the lens to its output surface. In some other embodiments, a proximal portion 1503a of the peripheral surface of the lens can have an elliptical shape (e.g., a portion extending from the input surface to the collar 1504), and a distal portion 1503b of the peripheral surface can have a different shape (e.g., a truncated conical shape)

In use, the input surface 1501 collects the light emitted by a light source coupled to the lens. A portion of the light enters the lens body via the central convex portion of the input surface and propagates to the output surface, typically without striking the peripheral elliptical surface. Another portion of the received light enters the lens body via the peripheral portion of the input surface and propagates to the peripheral elliptical surface to be reflected thereby toward to the output surface of the lens.

The lens 1500 can be formed of a variety of materials, such as a variety of polymeric materials. Some examples of suitable materials include polymethylmethacrylate (PMMA), polycarbonate, high density polyethylene, glass, etc.

The lens 1500 can be used in an optical assembly, such as the optical assembly discussed above in connection with FIG. 9. Further, similar to the previous embodiment, the lens 1500 can be embedded in a variety of different illumination devices, such as endoscopic systems.

Figure 12:
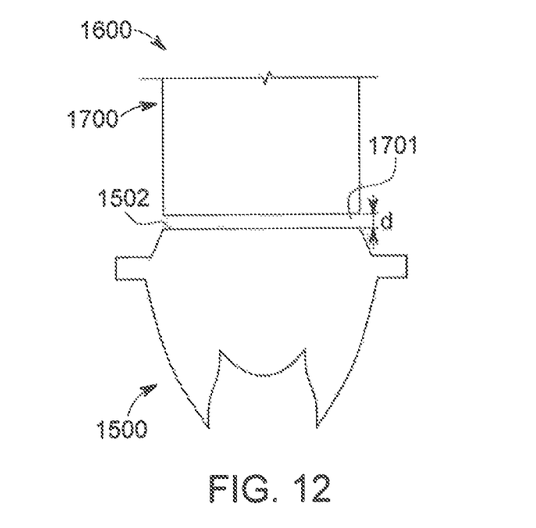
FIG. 12 is a schematic cross-sectional view of an optical assembly according to an embodiment in which a light guide is optical coupled to an output of a lens according to the present teachings.

FIG. 12 schematically depicts an optical assembly 1600, which includes the above lens 1500 optically coupled to a light guide 1700. In this embodiment, the input face 1601 of the light pipe is positioned at a distance (d) relative to the output surface 1502 of the lens. In other words, in this embodiment, the output surface of the lens is not in contact with the input face of the light pipe. Nonetheless, the output surface of the lens and the input face of the light pipe are sufficiently close to allow efficient coupling of the light exiting the lens into the light guide. In some embodiments, a spacer (not shown) can be used to fixedly hold the light guide a desired distance relative to the output surface 1502 of the lens. In some such embodiments, the output focus of the peripheral elliptical surface of the lens can be located in the gap separating the output surface of the lens from the input face of the light pipe.

A lens according to the present teachings, such as those described above, can have a variety of different sizes. For example the diameter of the lens output surface and its shape can be configured for efficient coupling of the lens to a light guide. By way of example, in some embodiments, such as those discussed above, the output surface of the lens can have a circular shape with a diameter in a range of about 1 mm to about 10 mm, though other sizes can also be employed. Further, the lenses according to the present teachings can be fabricated using known manufacturing techniques, such as molding, etc.

While several variations have been illustrated by way of example in particular embodiments, it is apparent that further embodiments could be developed within the spirit and scope of the present disclosure. However, it is to be expressly understood that such modifications and adaptations are within the spirit and scope of the present invention, and are inclusive, but not limited to the following appended claims as set forth.

What is claimed is:

1. An optical assembly, comprising:
   a lens having a lens body disposed about an optical axis, comprising:
      a proximal section, comprising at least one input surface having a convex central portion and a peripheral portion surrounding the convex central portion collectively forming a cavity for at least partially receiving light from a light source, and
      a distal section, comprising at least one output surface through which light exits the lens body; wherein a width of said distal section exhibits a decreasing taper from the proximal section to said at least one output surface through which light exits the lens body;
   a light guide optically coupled to the at least one output surface of the lens for receiving at least a portion of the light exiting the lens;
      wherein the proximal section further comprises a substantially elliptical peripheral surface for receiving at least a portion of the light entering the lens via the peripheral portion surrounding the convex central portion of the at least one input surface and for directing at least some of the received light via total internal reflection to the distal section, the substantially elliptical peripheral surface having proximal and distal focal points on the optical axis,
      wherein the proximal focal point is within the cavity and the distal focal point is positioned external to the lens and at a distance from the at least one output surface such that light rays diverging from the distal focal point exhibit an angular spread commensurate with a numerical aperture of the light guide.

2. The optical assembly of claim 1, wherein the light guide is attached to the output surface of the lens.

3. The optical assembly of claim 1, wherein the substantially elliptical peripheral surface transfers at least a portion of the light emitted by the light source from the proximal focal point to the distal focal point.

4. The optical assembly of claim 1, wherein the distance of the distal focal point relative to the output surface of the lens is in a range of about 4 mm to about 6 mm.

5. The optical assembly of claim 1, wherein the numerical aperture of the light guide has a value in a range of about 0.5 to about 0.9.

6. The optical assembly of claim 1, wherein at least about 90% of the received light at the one input surface is coupled into the lens.

7. The optical assembly of claim 1, further comprising a gap between the at least one output surface and the light guide fixed by a spacer material extended therebetween.

8. The optical assembly of claim 1, wherein the distal focal point is positioned outside of the distal section of the lens.

9. The optical assembly of claim 1, wherein the peripheral portion of the input surface is shaped such that at least a portion of the light entering the lens body via the peripheral portion propagates to the peripheral elliptical surface to be reflected thereby.

10. The optical assembly of claim 1, wherein the convex central portion is characterized by a positive optical power in a range of about 50 D to about 300 D.

11. The optical assembly of claim 1, wherein the peripheral portion of the input surface comprises a proximal concave segment and a distal convex segment.

12. The optical assembly of claim 1, wherein the input surface is configured to capture at least about 80% of the light emitted by the light source.

13. The optical assembly of claim 1, wherein the lens further comprises a collar encircling the lens body.

14. The optical assembly of claim 13, wherein the lens body and the collar are a unitary structure.

15. The optical assembly of claim 13, wherein any of the lens body and collar is formed of a polymeric material.

16. The optical assembly of claim 1, wherein the at least one output surface is substantially orthogonal to the optical axis.

17. The optical assembly of claim 1, wherein the peripheral portion of the input surface is shaped such that at least about 80% of the light entering the lens body via said peripheral portion propagates to the substantially elliptical peripheral surface of the lens body.

18. The optical assembly of claim 1, wherein at least a portion of the light entering the lens body via the convex central portion propagates to the at least one output surface.

19. The optical assembly of claim 1, wherein the convex central portion is configured such that the light entering said lens body via the convex central portion propagates to the at least one output surface without striking the substantially elliptical peripheral surface.

20. The optical assembly of claim 1, wherein said input surface is configured to capture at least about 90% of the light emitted by said light source.

21. The optical assembly of claim 1, further comprising an index matching material disposed between the at least one output surface and the light guide, wherein the index matching material is selected from the group consisting of a liquid, a gel, and an adhesive.

22. The optical assembly of claim 1, wherein the distal focal point is positioned within the light guide.

23. An optical assembly, comprising:
a lens having a lens body disposed about an optical axis, comprising:
a proximal section, comprising at least one input surface having a convex central portion and a peripheral portion surrounding the convex central portion, wherein said convex central portion and said peripheral portion surrounding the convex central portion collectively form a cavity for at least partially receiving light from a light source, wherein the peripheral portion of the input surface is shaped such that at least about 80% of the light entering the lens body via the peripheral portion propagates to the peripheral surface of the lens body; and
a distal section, comprising at least one output surface, wherein a width of the distal section exhibits a decreasing taper from the proximal section to the at least one output surface through which light exits the lens body;
a light guide optically coupled to the at least one output surface of the lens for receiving at least a portion of the light exiting the lens;
wherein the proximal section further comprises a substantially elliptical peripheral surface for receiving at least a portion of the light entering the lens via the peripheral portion surrounding the convex central portion of the at least one input surface and for directing at least some of the received light via total internal reflection to the distal section.

24. The optical assembly of claim 23, wherein said substantially elliptical peripheral surface comprises a proximal focal point disposed within said cavity and a distal focal point that is positioned external to the lens and at a distance from said at least one output surface such that light rays diverging from the distal focal point exhibit an angular spread commensurate with a numerical aperture of the light guide.

\* \* \* \* \*